United States Patent
Krause et al.

(10) Patent No.: US 6,489,516 B1
(45) Date of Patent: Dec. 3, 2002

(54) PROCESS FOR THE ETHERIFICATION OF OLEFINS

(75) Inventors: Outi Krause, Espoo (FI); Reetta Karinen, Espoo (FI)

(73) Assignee: Fortum Oil and Gas Oy, Espoo (FI)

( * ) Notice: Subject to any disclaimer, the term of this patent is extended or adjusted under 35 U.S.C. 154(b) by 0 days.

(21) Appl. No.: 09/958,748

(22) PCT Filed: Apr. 13, 2000

(86) PCT No.: PCT/FI00/00313

§ 371 (c)(1),
(2), (4) Date: Oct. 12, 2001

(87) PCT Pub. No.: WO00/61533

PCT Pub. Date: Oct. 19, 2000

(30) Foreign Application Priority Data

Apr. 13, 1999 (FI) ................................................ 990809

(51) Int. Cl.$^7$ .............................................. C07C 41/06
(52) U.S. Cl. ......................... 568/697; 525/291; 525/242
(58) Field of Search .......................... 568/697; 525/291, 525/242

(56) References Cited

U.S. PATENT DOCUMENTS

| 5,244,929 A | 9/1993 | Gottlieb et al. ................ 521/29 |
| 5,415,908 A | 5/1995 | Näsman et al. ............. 428/36.2 |
| 5,798,417 A | 8/1998 | Howard, Jr. ................. 525/276 |

FOREIGN PATENT DOCUMENTS

| EP | 0 629 441 A1 | 12/1994 | ............ B01J/31/06 |

*Primary Examiner*—Rosalynd Keys
(74) *Attorney, Agent, or Firm*—Birch, Stewart, Kolasch & Birch, LLP

(57) ABSTRACT

The present invention concerns a process for the etherification of olefins. According to the process, an olefin or a mixture of olefins is reacted with an alcohol or a mixture of alcohols in the presence of a catalyst. According to the invention, a catalyst is used which comprises a grafted polymer fiber, there being functional groups attached to the grafted polymer fiber. By means of the invention it is possible to speed up the etherification process of, in particular, heavier ethers.

10 Claims, No Drawings

PROCESS FOR THE ETHERIFICATION OF OLEFINS

This application is the national phase under 35 U.S.C. §371 of PCT International Application No. PCT/FI00/00313 which has an International filing date of Apr. 13, 2000, which designated the United States of America and was published in English.

The present invention relates to the preparation of ethers. The invention relates in particular to the etherification process for the etherification of an olefinic hydrocarbon feed, according to which process the olefin or mixture of olefins is reacted with an alcohol or mixture of alcohols in the presence of a catalyst, characterized in that a catalyst is used which comprises a grafted polymer fiber, there being functional groups attached to the grafted polymer fiber.

According to such a process, the olefins of an olefinic hydrocarbon precursor, in particular $C_8 \ldots C_2$ olefins, are reacted with a suitable alcohol in the presence of a catalyst in order to produce corresponding ethers. The reactions can be carried out in a stirred reactor, a fixed-bed reactor, a fluid-bed reactor, a tubular reactor or a catalytic distillation column. These ethers are recovered, and they are treated further when necessary in order to prepare engine fuel components.

The invention also relates to the use of the fiber catalyst as an etherification catalyst, which has been grafted and to which grafted polymer fiber there are attached functional groups, as an etherification catalyst.

Tertiary ethers are compounds used as components in gasoline, having many properties which improve the quality of gasoline. Being oxygen-containing compounds they enhance the combustion of the fuel and thus reduce emissions from traffic. Owing to their high octane number they replace in gasoline lead and aromates, which have previously been used for increasing the octane number. By means of etherification it is also possible to decrease the concentration of olefin in gasoline. It is expected that in the future the use of ethers as gasoline components will increase along with emission restrictions and legislation concerning the environment. Methyl-tert-buty ether MTBE and tert-amyl-methyl ether TAME are the most commonly used gasoline ethers, but continuous research is also being carried out into new tertiary ether molecules. It is also expected that in the future new ethers, having molecule sizes greater than have conventional ethers, will gain a foothold on the market.

In the preparation of tertiary ethers there have been used as catalysts, for example, zeolites, heteropolyacids and their salts, silicates and clays modified in different ways, and homogenous acid catalysts. In commercial applications, however, strongly acid cationic ion exchange resins are used almost without exception.

Ion exchange resins are by their basic structure styrene and divinyl benzene copolymers sulfonated with sulfuric acids. The active sites of the catalyst are made up precisely of these hydrogen ions of the acid. The catalyst particles are spherical in shape, and their diameters range typically from 0.3 to 1.0 mm. The sulfonic acid groups are evenly distributed over the entire catalyst particle, and in order for the reaction to take place, the starting materials of the reaction must pass to the active sites of the catalyst.

In ion exchange resin catalyst particles the components must thus first pass from the bulk solution to the catalyst particle. Thereafter the components must further pass under the effect of diffusion to the catalyst's active sites, where the reaction occurs. Also, the reaction products must pass, under the effect of diffusion, out of the pores of the catalyst particle, and further back into the bulk solution.

In spherical porous particles the distances become large. The tertiary olefins used as the precursors in the etherification reaction, as well as the product components, ethers, are by structure branched products. The larger and the more branched the molecules which are being etherified, the more difficult and slower is the passage of the component in the pores of the catalyst particle. In fact, a situation is approached in which the total rate of reaction is determined by the mass transfer, i.e. the rate of diffusion, and no longer by the rate of the chemical reaction.

Also cross-linking, which is an important variable for resin particles in terms of the structure, stiffens the structure of the resin and thereby renders the diffusion of the components in the pores of the catalyst particle more difficult. Resin catalysts are indeed quite complicated in structure. Changes in the conditions easily cause changes in the catalyst structure. Furthermore, the ion exchange resin matrix swells under the effect of polar substances. For example, methanol, which is often used as a starting material in etherification, is strongly polar. The effect of swelling on the number and quality of the active sites in a catalyst is not precisely known, but as the matrix swells the concentration of the polar component increases and the mass transfer of the other components in the pores of the catalyst is probably slowed down further.

Publication EP-A-629 441 describes the preparation of a fibrous polyethylene or polypropylene catalyst. The said catalysts were packed in a net-like fabric before they were used. The publication reports that the object is to prepare a catalyst the active sites of which are easily accessible, but does not discuss in detail the potential uses of the catalyst except that they can be used in organic syntheses.

The object of the present invention is to eliminate the problems of the prior art and to provide an entirely novel process for the preparation of ethers.

The invention is based on the idea that olefins, in particular branched $C_8-C_2$ olefins, are reacted with alcohol in the presence of a fibrous catalyst. The catalyst is based on a polyolefin backbone to which a compound which contains reactive groups is grafted, whereafter a functional group is introduced into the fibrous structure. Surprisingly, the catalyst according to the invention has been found to be highly reactive, in particular in the etherification reaction of heavier olefins and methanol. The use of the fiber improves the rate of the reaction as compared with known catalysts, in particular when the molecule size of the ether being produced increases, whereupon the difference from conventional etherification catalysts is considerable.

More precisely, the process according to the invention is characterized by the etherification of an olefinic hydrocarbon feed, according to which process the olefin or mixture of olefins is reacted with an alcohol or mixture of alcohols in the presence of a catalyst, characterized in that a catalyst is used which comprises a grafted polymer fiber, there being functional groups attached to the grafted polymer fiber.

The catalytic properties of the catalyst according to the invention are highly similar to those of conventional ion exchange resins, but owing to its structure its mass transfer properties differ from those of ion exchange resins. The active sites of the catalyst are on the catalyst surface, and mass transfer to the fiber surface is significantly easier than into the pores of a spherical catalyst particle. On the other hand, the catalytically active sulfonic acid groups are located in a side chain of the polymer, and the side chains of the polymer are not cross-linked in the catalyst according to the invention. Thus the mobility of the side chains is greater than in ion exchange resin particles, and the diffusion resistance to the passage of components is, even on account of this fact, less than in ion exchange resins.

When, according to the invention, a fiber catalyst is used in etherification, higher rates of reaction are achieved and thus shorter residence times in the reactors are made possible. Thus it is possible to speed up the etherification process and thereby to increase production. The advantages of the invention are especially prominent when there are produced ethers having more than 6 carbon atoms, and in particular when there are 9–10 carbon atoms. According to the invention, the catalyst can also be used in the reaction in the form of a slurry, since the good filterability of the fibers ensures that the fibers are easily separated from the reaction solution. Even in other respects, processing with fibers is easy, since the mechanical strength of the fibers is good. It can be noted further that in the conditions used the fibers are also chemically stable.

The fiber catalysts used in the invention are supplied by, for example, Smoptech Oy. Table 1 shows a summary of the properties of the Smopex-101 fiber catalyst manufactured by Smoptech Oy and the conventional commercial ion exchange resin Amberlyst 35 (Rohin & Haas).

TABLE 1

Properties of Smopex-101 fiber catalyst and a conventional resin catalyst (Amberlyst 35)

|  | Smopex-101 | Amberlyst 35 |
| --- | --- | --- |
| Form | fiber | sphere |
| Size | length 4 mm diameter approx. 30 μm | diameter 700–950 μm |
| Capacity (mmol/g) | 1–4 | 5.2 |
| Active group | sulfonic acid | sulfonic acid |
| Specific surface area (m$^2$/g) | 0.15 | 45 |

As is shown in the table, the properties of the fiber catalyst according to the invention and conventional resin catalysts cannot be compared directly with each other, because of structural differences, for example, the specific surface area and the dimensions of the catalyst are not comparable.

The catalyst used in the invention is typically made up of polymer fibers grafted with a compound which contains reactive groups. The polymer fiber is, for example, of a polyolefin or a polyolefin which contains fluorine. Preferably there is used a homo- or copolymer of polyethylene or polypropylene or a fluorine-containing ethylene or propylene, of which the homo- and copolymers of polyethylene are regarded as especially suitable for the present invention.

The compound which contains reactive groups usually comprises at least one double bond. Preferably the reactive group is styrene or a derivative thereof.

A functional group is introduced into the grafted polymer fiber. The functional group applicable to the catalysis of the etherification reaction is an acid group; preferably sulfonic acid groups are used. When a grafted polyolefin fiber is sulfonated using chlorosulfonic acid, the catalytically active sulfonic acid groups attach specifically to the reactive groups of the side chains. During the preparation of the fibers the sulfonic acid content of the catalyst and thereby the ion exchange capacity can be regulated, and thus the properties of the catalyst can be tailored according to the need at a given time. An especially advantageous catalyst in the context of the present invention is a styrene-grafted and sulfonated polyethylene fiber.

It is also possible to graft a polymer fiber with a monomer which already contains a functional group.

The diameter of the catalyst fibers is typically approx. 20–40 μm, most commonly approx. 30 μm, and their length approx. 1–10 mm, preferably 3–4 mm.

The catalyst may be in the reactor in the form of a slurry, in which case it is fed into the reactor as such or can be fixed in place in any manner, known per se, which restrains the movement of the catalyst fibers. If the catalyst is in the form of a slurry, it is separated from the reaction solution after the reaction, for example by filtration. In a continuous-working process it is preferable to fix the catalyst in place.

According to the invention, olefins are reacted with alcohol. The reactor feed may be made up either of one specific olefin or of a mixture of one or more olefins. The olefins may be branched or linear. Preferably there are used branched $C_{4-C_{12}}$ olefins the linear carbon backbone of which comprises a chain of 3–11 carbon atoms. Especially preferably there are used branched $C_{8-C_{10}}$ olefins the linear carbon backbone of which comprises a chain of 5–6 carbon atoms. This chain of carbon atoms has at least one double bond, at least one of the carbon atoms connected by the bond being substituted in such a manner that there is not a single hydrogen atom linked thereto. The oxygen atom of the alcohol attaches to this carbon atom, whereby an ether is formed. The rest of the olefin backbone may be branched or linear. The substituent may be any hydrocarbon chain. Very branched substituents in the substituted carbon atom of the double bond may cause steric hindrance to the access of the oxygen atom to the carbon atom, and thus preferably the substituent of the substituted carbon atom of the double bond is a straight-chain hydrocarbon group, and most typically it is a methyl group.

2,4,4-trimethyl-1-pentene and 2,4,4-trimethyl-2-pentene can be mentioned as examples of olefins highly suitable for etherification according to the invention.

In the etherification, the alcohol used is preferably methanol, but other alcohols, typically $C_{2-C_8}$ alcohols can also be used. In particular alcohols in which the OH group is at the end of a straight carbon chain, such as ethanol, propanol and butanol, are good options, but also alcohols in which the carbon chain is branched can be used in etherification according to the invention. On the other hand, alcohols in which the OH group is located in the carbon chain, such as 2-propanol, can well also be used. The alcohol feed may also be a mixture of several different alcohols. The best etherification result is, of course, achieved using as pure alcohol as possible, but on an industrial scale it is well possible to use an alcohol of a low degree of purity, although in general water is removed from the alcohol feed.

The starting materials are fed into the reactor typically at a molar ratio of 0.1:10–10:0.1, preferably 0.5:5–5:0.5. The etherification is carried out at a temperature of approx. 50–120° C. preferably within the range of 70–90° C. Since the etherification reaction is slow, it is recommendable to use high temperatures, although the thermal stability of the catalyst used in each given case is to be taken into account. The reactor used may be a continuously operated or batch or semi-batch stirred reactor, fixed-bed reactor, fluid-bed reactor, tubular reactor or catalytic distillation column.

The use of overpressure in the etherification reactor enables the use of higher temperatures, since, owing to the overpressure, the alcohol and olefin as well as the reaction product formed can be kept in the liquid phase. The required overpressure thus depends on the reaction components and the temperature used. At the temperatures used in connection with the present invention, preferably at least a slight overpressure is used in order that all of the reaction component should remain in the liquid phase. Typically the pressure in the reactor is below 20 bar.

The following examples illustrate the technical solution according to the invention.

EXAMPLE 1

A mixture of 2,4,4-trimethyl-1-pentene and 2,4,4-trimethyl-2-pentene (Fluka Chemica AG, 95%, isomer ratio 3.5) was etherified with methanol (Riedel-de Haën, >99.8%) in a batch reactor by using 1.0 g of Smopex-101 catalyst. The molar ratio of methanol to olefins was 1:1. The reaction was carried out at a temperature of 80° C. and a nitrogen pressure of 8 bar. The catalyst was compared with Amberlyst 35, a commercial ion exchange resin catalyst (Rohm & Haas), by means of which a corresponding run was carried out using 1.3 g of catalyst. The initial rate of ether formation per the number of acid sites in the catalyst, i.e. its ion exchange capacity, was calculated from each catalyst. At 80° C. the initial rate obtained with Smopex-101 catalyst was 1.3 mmol/(s equiv.) and with Amberlyst 35 it was 0.3 mmol/(s equiv.) The difference in the initial rates of the catalysts was thus approx. four-fold.

EXAMPLE 2

Isoamylene, i.e. a mixture of 2-methyl-1-butene and 2-methyl-2-butene, (Fluka Chernica AG, 2-methyl-2-butene tech. 85%, isomer ratio 1:9) was etherified with methanol (Riedel-de Haën, >99.8%) to tet-amyl-methyl ether, i.e. TAME, by using 1.0 g of Smopex-101 catalyst. In the feed the molar ratio of methanol to isoamylene was 1:1. The reaction was carried out at 80° C. and 8 bar, and the initial velocity of ether formation was calculated per the number of acid sites in the catalyst, i.e. its ion exchange capacity. At a temperature of 80° C., the initial velocity obtained with Smopex-101 catalyst was 0.5 mmol/(s equiv.).

What is claimed is:

1. A process for the etherification of an olefinic hydrocarbon feed, according to which process the olefin or mixture of olefins is reacted with an alcohol or mixture of alcohols in the presence of a catalyst, characterized in that a catalyst is used which comprises a grafted polymer fiber, there being functional groups attached to the grafted polymer fiber, the olefin is a substituted hydrocarbon in which at least one of the carbons linked to each other with a double bond is substituted in such a manner that there is not a single hydrogen atom linked to the said carbon atom, and wherein the functional groups are located in a side chain of the grafted polymer fiber and the side chains are not cross-linked in the catalyst.

2. The process according to claim 1, characterized in that the catalyst comprises a polymer fiber grafted with a compound which contains reactive groups, there having been functional groups introduced into the grafted polymer fiber.

3. The process according to claim 1 or 2, characterized in that the polymer fiber is a homo- or copolymer of polyethylene.

4. The process according to claim 2, characterized in that the compound which contains reactive groups is styrene.

5. The process according to claim 1, characterized in that the functional group is an acid group.

6. The process according to claim 1, characterized in that the olefin is a substituted hydrocarbon the linear carbon backbone of which comprises 3–11 carbon atoms.

7. The process according to claim 6, characterized in that the olefin is 2,4,4-trimethyl-1-pentene or 2,4,4-trimethyl-2-pentene.

8. The process according to claim 1, characterized in that the alcohol is methanol.

9. The process according to claim 5, wherein the functional group is a sulfonic acid group.

10. The process according to claim 6, wherein the olefin is a substituted hydrocarbon the linear carbon backbone of which comprises 5–6 carbon atoms.

* * * * *